United States Patent [19]

Comeau

[11] Patent Number: 4,572,173
[45] Date of Patent: Feb. 25, 1986

[54] CLEAN CAP

[76] Inventor: Perry J. Comeau, Rte. 3, Box 15, Valley Dr., Searcy, Ark. 72143

[21] Appl. No.: 614,567

[22] Filed: May 29, 1984

[51] Int. Cl.[4] ............................................. A61F 13/00
[52] U.S. Cl. ............................. 128/132 D; 128/163; 2/202; 2/DIG. 7
[58] Field of Search ............... 128/132 D, 132 R, 163; 2/9, 10, 171, 171.5, 173, DIG. 7, 202, 410, 206, 203, 417

[56] References Cited

U.S. PATENT DOCUMENTS

| | | | |
|---|---|---|---|
| 3,872,516 | 3/1975 | Bird et al. | 2/202 |
| 3,885,558 | 5/1975 | Belkin | 2/173 |
| 3,943,575 | 3/1976 | Bolker | 2/DIG. 7 |
| 4,331,136 | 5/1982 | Russell et al. | 128/163 |
| 4,457,026 | 7/1984 | Morris | 128/132 D |

FOREIGN PATENT DOCUMENTS

| | | | |
|---|---|---|---|
| 420634 | 2/1911 | France | 2/203 |
| 746876 | 6/1933 | France | 128/163 |
| 555541 | 8/1943 | United Kingdom | 128/163 |

*Primary Examiner*—Gene Mancene
*Assistant Examiner*—Cary E. Stone
*Attorney, Agent, or Firm*—Head, Johnson & Stevenson

[57] ABSTRACT

A clean cap for covering the head of a patient on an operating table to provide warmth and to prevent blood from contaminating the patient's hair, the cap being formed of a unitary piece of flat material foldable around the patient's head, having fasteners for holding the cap in place. Adhesive secured to the edge of the material seals against the skin of the patient to prevent blood flowing into the area under the cap.

6 Claims, 9 Drawing Figures

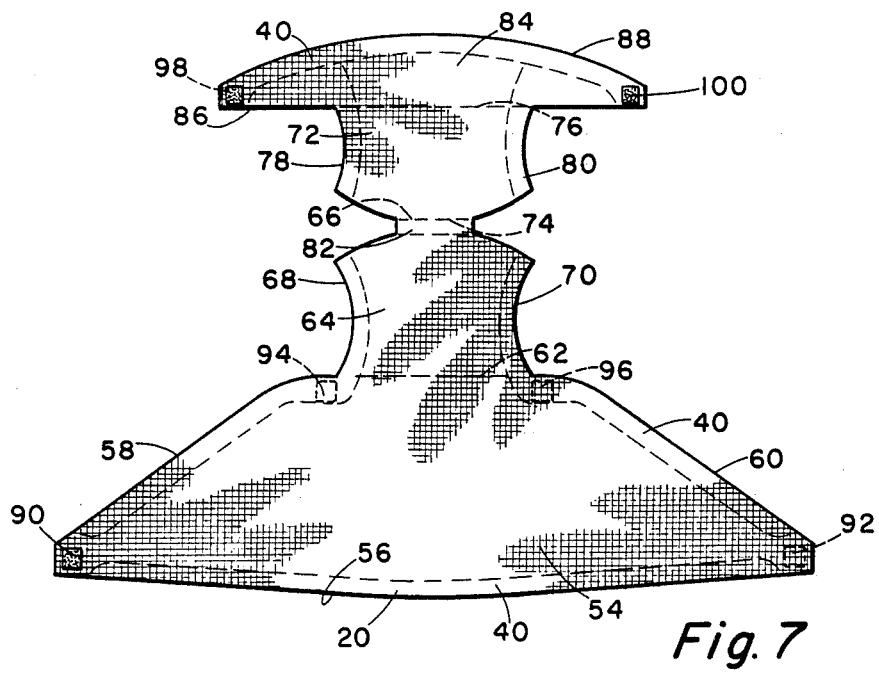
Fig. 7
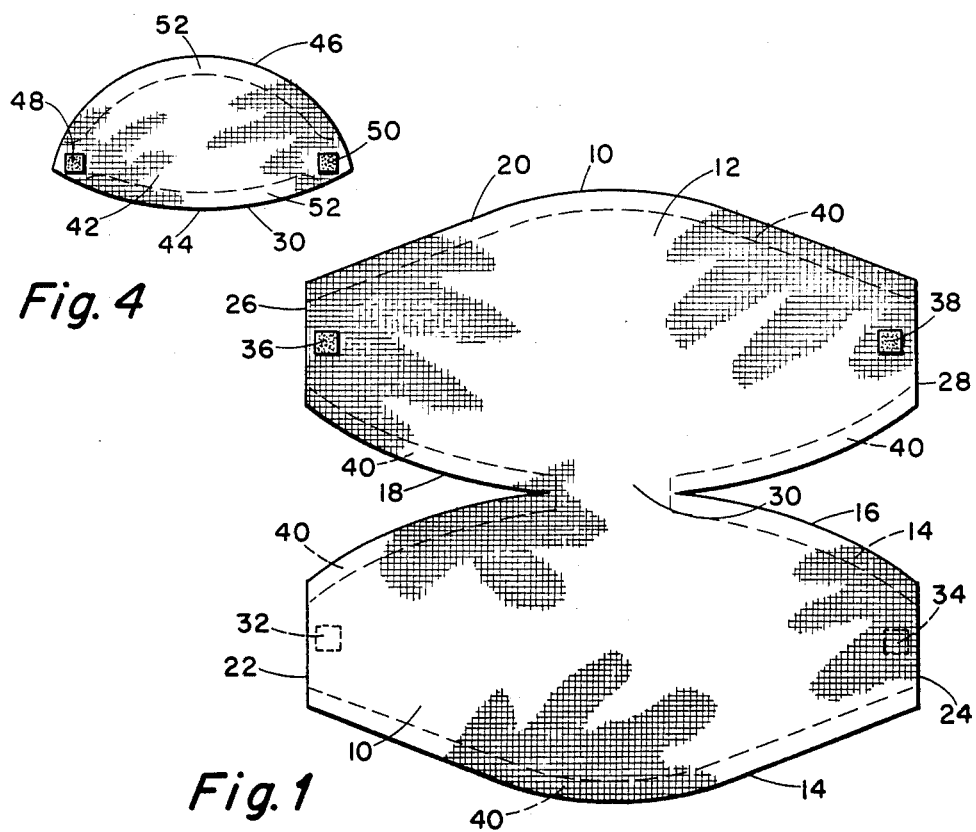
Fig. 4
Fig. 1

CLEAN CAP

SUMMARY OF THE INVENTION

This invention relates to a cap to be worn by patients during operating procedures. More specifically, the invention relates to a flat piece of material such as of paper, cloth or plastic, or combinations of these materials, with adhesive bands and fasteners that act to keep the patient's head warm and to prevent the patient's hair from being contaminated with blood.

Various devices have been created for protecting the head against the weather elements or covering the hair of users for the application of lotion or dyes to the hair so as to shield the face and the rest of the body from contact with these lotions and dyes. Other devices have been designed such as caps used in bathing or swimming activities which seal the hair off from contact with water. The Spiegel U.S. Pat. No. 2,507,386 recites a hair treating apparatus consisting of a double-walled cap fitting snugly over the users head. However, this invention is primarily adapted to receive fluid to be distributed to the roots of the hair and scalp thus requiring it to fit tight on the head to prevent the escape of excess liquid. The device is not easily inserted on or removed from the user and thus is not adaptable for hospital operating applications. The present invention provides a cap which is not constructed to fit snugly on the head but to be sealed at the edges in order to prevent the patient from being contaminated with blood during an operation. Further, an important aspect to the present invention is to provide warmth to the patient during operating procedures.

The Greenhouse U.S. Pat. No. 3,447,164 is also unlike the present invention in that one of its primary purposes is to provide a water tight seal by way of plurality of small, balloon-like members in closely adjacent staggered rows. This type cap is difficult to put on and take off of a patient and therefore is not adaptable for operating room uses.

The Weiker U.S. Pat. No. 2,704,846 also recites a relatively tight cap using tie-straps to secure firmly to the head to protect the wearer from a bathroom shower spray, or to retain moist conditions such as when receiving a permanent. This device is primarily characterized by its compact use for travel; however, it like the other references mentioned above, is not easy to put on or take off a patient and thus is not adapted for hospital room use. Further, it is not intended to provide warmth for a patient.

Contrary to the type of caps revealed in the prior art, such as those prior issued United States Patents mentioned above, the present invention provides a cap for easily placing on or taking off a patient during hospital room operating procedures. Most hospital rooms are kept relatively cool so as to prevent surgeons and assistants from perspiring, which perspiration can cause fogging of glasses thus obscuring vision or drip into open incisions. While the cool temperatures are advantageous for the workers in an operating room it can be deleterious to the patient, since a patient under anesthesia is not well equipped to respond to permit the body's mechanisms to maintain proper body temperature. Further, since portions of the patient being operated on must be freely exposed it is impractical to cloth patients with warm clothing. The present invention provides a simple and inexpensive means of protecting the head of a patient during operating procedures. In addition the invention provides means of preventing blood from contaminating the hair of the patient. Coagulated blood in hair is difficult and time consuming for hospital personnel to remove, especially when it needs to be performed immediately after an operation while the patient is in the recovery mode.

The invention includes a cap formed of a piece of flat, flexible material which may be absorbant paper, cloth, plastic, or a combination of these elements. The flat piece of material is cut into a prescribed shape which can be expeditiously folded around the head of the patient. Attachment means, such as Velcro type devices, are affixed to the cut-out portions of the cap so that as the cap is folded around the patient's head it is readily retained in position.

Bands of adhesive material are formed on the edges of the flat cut-out cap member so that when the cap member is folded onto the patient's head and the connection device is affixed to retain the cap in position, the adhesive material may be pressed against the skin around the edges to retard the passage of blood and thus prevent contamination of the patient's hair.

The material of which the cap is formed should be such as to retain heat so as to provide warmth for the patient. The insulative material of which the cap is made may be of the type having captured air bubbles, and the size of the air bubbles may be progressive.

In a second embodiment of the invention a separate eye piece is employed which may be attached to the cap to shield the eyes and the bridge of the nose of the user. This is important in some type of procedures wherein a sheet placed over the face of the patient can cause corneal abrasion since a patient under anesthesia may have his eyes open and is thus subject to contact by a sheet covering the patient's face.

The cap may come in a variety of sizes, including sizes to fit infants. Providing warmth is particularly important for infants. The cap of this invention may be formed of flat sheets of material and is foldable about the head of the patient. It may be manufactured, distributed and stored in the flat form. The cap can, as an alternate arrangement, be partially pre-molded after being cut so as to fit the patient's head with fewer pleats and wrinkles.

A better understanding of the invention will be had by reference to the following description and claims, taken in conjunction with the attached drawings.

DESCRIPTION OF THE DRAWINGS

FIG. 1 is a plan view of material cut to form a cap according to this invention.

FIG. 4 is a plan view of a supplemental eye shield piece which may be employed with the cap of FIG. 1.

FIG. 7 is a plan view of an alternate design of a cap for use on patients during surgical procedures, the design being cut from flat flexible material.

DESCRIPTION OF THE PREFERRED EMBODIMENT

Figure 8:
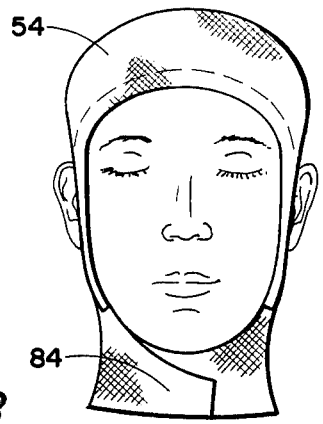
FIG. 8 is a front elevational view of a patient having the cap of FIG. 7.

Referring to the drawings and first to FIG. 1, an embodiment of the invention is illustrated. FIG. 1 shows a cap which has been cut from a flat sheet of flexible material. The flexible material may be absorbant paper, cloth, plastic, or a combination of these materials. The flat sheet is cut to form a first portion 10 and a second portion 12. The first portion 10 and second portion 12 are of the same shape and each portion is formed of opposed elliptical edges, the edges of first portion 10 being identified by the numerals 14 and 16 and the edges of second portion 12 being identified by the numerals 18 and 20. The elliptical edges are joined by opposed sides, the first portion 10 having sides 22 and 24 and the second portion 12 having sides 26 and 28. The sides are spaced apart and parallel to each other.

The edge 16 of first portion 10 is joined to the edge 18 of second portion 12 at 30 forming a narrow connecting linkage between the two portions.

Attachment elements 32 and 34 are secured to the bottom surface of first portion 10 adjacent the sides 22 and 24. In a similar manner, attachment elements 36 and 38 are secured to the top surface of portion 12. These attachment elements may preferably be of the Velcro type, a type of fastener commonly used for securing flexible materials such as clothing, in which a plurality of small plastic hooks removably engage a felt-like surface so that the portions of the attachment means when pressed together remain in such position but can be separated by direct pull.

Figure 2:
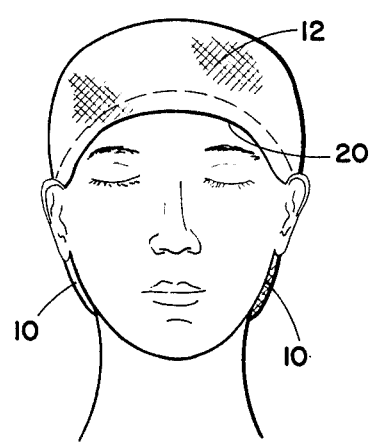
FIG. 2 is a front elevational view of the cap formed as in FIG. 1 positioned on a patient as used during an operating procedure.
Figure 3:
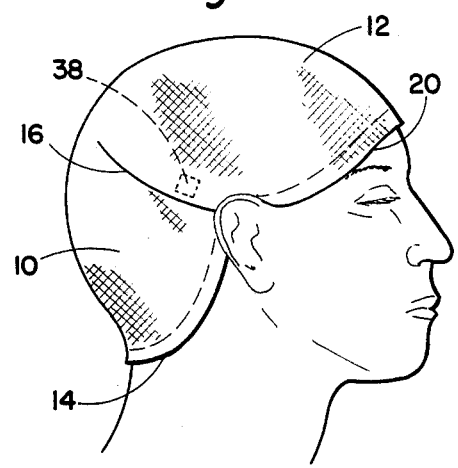
FIG. 3 is a side view of the cap formed of the device of FIG. 1 positioned on a patient.

FIGS. 2 and 3 show the apparatus of FIG. 1 on the head of a patient. The first portion 10 fits against the back and upper neck of the patient and the second portion 12 fits over the top and forehead of the patient. The attachment elements are secured to each other, attachment element 38 being now on the underneath side of the second portion 12 as shown in FIG. 3 and is secured to attachment portion 34, although the portion 34 is not seen in FIG. 3. In like manner, attachment portion 36 engages attachment element 32 on the opposite side of the head of the user.

The cap as shown in FIGS. 2 and 3 serve to keep the patient's head warm during operating procedures, the importance of which has been previously discussed. In addition, the cap serves to keep blood, which may result from the operating procedures, from coming into contact with the patient's hair and thus greatly simplifies cleaning up the patient after an operation. To more securely seal against contamination of the patients hair with blood, a preferred arrangement includes the provision of adhesive strips 40 placed on both the first and second portions 10 and 12 along the elliptical edges 14, 16, 18 and 20. When the cap is placed on the head of the user the adhesive strips 40 are employed to retain the edges in firm engagement with the skin of the patient so as to reduce the possibility of blood passing under the cap and into the hair of the patient.

FIG. 4 shows an additional element which may be employed with the invention. It is an eye shield portion 42 formed of a flat material and defined by opposed elliptical edges 44 and 46. The eye shield also having attachment means 48 and 50 and adhesive bands 52 adjacent the elliptical edges 44 and 46.

Figure 5:
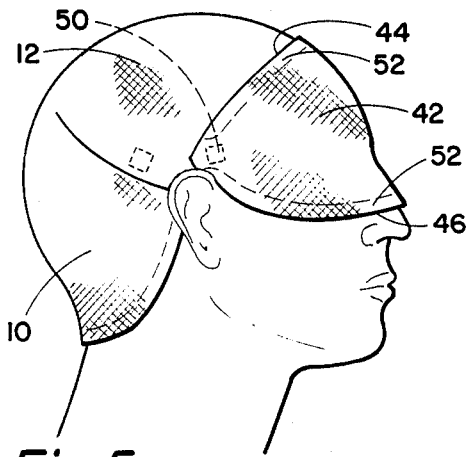
FIG. 5 is an elevational side view of a patient with a cap of FIG. 1 and with an eye shield of FIG. 4.
Figure 6:
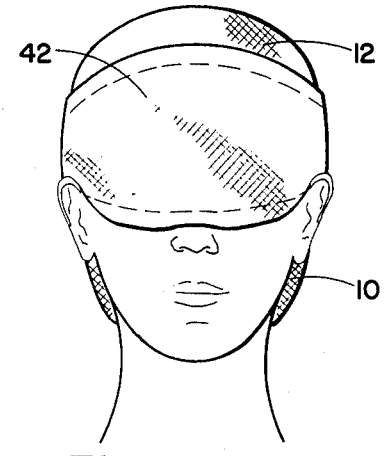
FIG. 6 is a front view of the patient of FIG. 5.

FIGS. 5 and 6 show the cap of FIG. 1 and the eye shield of FIG. 4 in position on a patient. The eye shield 42 fits over the eyes, forehead and bridge of the nose of the user and is secured in place by the attachment elements 48 and 50. The eye shield 44 serves to provide further warmth for the patient and, in addition, is exceedingly valuable in preventing corneal abrasion of the patient by shielding the patient's eyes from a sheet or other covering which may be placed over the patient during operating procedures.

FIG. 7 shows an alternate embodiment of the invention. This embodiment is of a similar principal but is of a more complex structure. Like FIG. 1, the embodiment of FIG. 7 is cut from a flat sheet of flexible material and includes a first generally frustrotriangular portion 54 having a generally straight first edge 56, equal length inwardly side edges 58 and 60, and an imaginary second edge 62 which is generally parallel to the first edge 56. Integrally connected to the first portion 56 is a second, generally rectangularly shaped portion 64 having an imaginary first edge which is coincidence with edge 62 and having a second edge 66 which is partially imaginary, the second edge being spaced, and generally parallel the first edge 62. The edges 62 and 66 are connected by side edges 68 and 70.

A third generally rectangular portion 72 has a first edge 74, a portion of which is imaginary and an opposed parallel imaginary edge 76 and opposed side edges 78 and 80.

A fourth flap portion 82 is of a relatively small width and length and serves to integrally connect the second portion 64 with the third portion 72 and has, at each end thereof, imaginary edges 66 and 74.

A fifth portion 84 has a first edge 86, a portion of which is coincidence with the imaginary edge 76, and a second edge 88 which is generally elliptical.

The embodiment of FIG. 7 has attachment elements 90 and 92 at the opposed ends of first portion 54; attachment elements 94 and 96 adjacent the outer ends of second imaginary edge 62; and attachment elements 98 and 100 adjacent the ends of the fifth portion 84. Like the embodiment of FIG. 1, the embodiment FIG. 7 has adhesive edges or strips 40 around the periphery.

Figure 9:
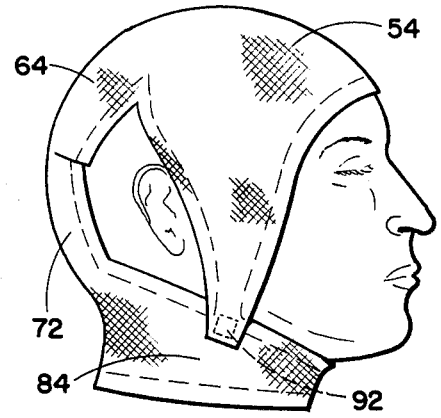
FIG. 9 is a side elevational view of the patient of FIG. 8 with the cap of FIG. 7.

FIGS. 8 and 9 show the device of FIG. 7 positioned on a patient's head with the attachment serving to hold it in position. The first portion 54 fits over the top and forehead of the patient and down along the sides of the face with the second portion 64 covering the back of the head and with the third portion 72 and fifth portion 84 covering the lower back and neck.

The cap of this invention, whether the embodiment of FIG. 1 or FIG. 7 may be made in a variety of sizes to cover patients from neonatal to full adults. The specific geometrical arrangement of the cap can vary from the illustrated designs to achieve certain benefits such as whether the ears of the patient are to be covered, how much of the forehead is to be exposed, how much of the neck and throat is to be covered and so forth and for this reason it can be understood that the actual practice of the invention may employ the principles hereof but with caps being constructed of materials cut from flat flexible sheets wherein the pattern varies from those illustrated.

In order to more perfectly fit the cap to the patient it may be preformed or shaped so that instead of being delivered as folded flat articles it may be configured to conform, at least in part, to the head of the user.

The cap serves the dual function of first, providing warmth and protection for the patient and, second, serves to guard against excessive flow of blood to mat in the hair of the patient. Due to the exceeding inexpensive arrangement of the cap, it can be a one-time use item that, after the operating procedures is terminated it can be removed from the patient and discarded.

While the invention has been described with a certain degree of particularity, it is manifest that many changes may be made in the details of construction and the arrangement of components without departing from the spirit and scope of this disclosure. It is understood that the invention is not limited to the exemplified embodiments set forth herein but is to be limited only by the scope of the attached claim or claims, including the full range of equivalency to which each element thereof is entitled.

What is claimed is:

1. A cap for use on patients, such as during surgical procedures, to provide warmth and cleanliness comprising:
   a unitary piece of flat flexible material defined by;
   a first generally frustro-triangular portion having a generally straight first edge, equal length inwardly tapered sides and an imaginary second edge generally parallel the first edge;
   a second generally rectangularly shaped portion, having an imaginary first edge coinciding with said first portion imaginary second edge and having a second edge generally parallel and spaced from the first edge, and having opposed side edges;
   a third generally rectangular portion having a first edge and an imaginary second edge and opposed side edges;
   a fourth, flap portion of relatively small width and length integrally connection said second edge of said second portion and said first edge of said third portion;
   a fifth generally triangular shaped portion having a first edge, the intermediate portion of which is coincident with said third portion imaginary second edge, and having an elliptical second edge; and
   attachment means at the outer ends of said first portion first edge, at the ends of said first portion second edge, and at the ends of said fifth portion first edge, whereby the cap may be fit on the head of patient with said fifth portion extending around the neck of the patient, the third portion fitting on the lower back portion of the patients head, the second portion extending over the upper back portion of the patients head and said first portion fitting on top of the patient's head, the attachment means serving to hold the portions in assembled relationship on the patient's head.

2. A clean cap according to claim 1 including adhesive strips affixed to said first portion first edge and tapered sides, said second portion side edges, said third portion side edges and said fifth portion elliptical edge, the adhesive strips serving to adhere to the skin of the patient receiving the cap to reduce blood passing underneath the cap.

3. A clean cap according to claim 1 wherein said attachment means are of the Velcro type.

4. A cap for use on a patient to provide warmth and cleanliness such as during surgical procedures comprising:
   a unitary piece of flat flexible material defined by;
   a first portion and a second portion of generally the same configuration, each portion having a first and a second spaced apart generally elliptical edge, the first and second edges being joined by spaced apart, parallel side edges, the first and second edges being furthest apart intermediate the side edges, said first and second portions being integrally joined at the intermediate portion of said first portion second edge and said second portion first edge; and
   attachment elements affixed to said first and second portions adjacent each of said side edges, whereby said unitary piece may be formed onto the head of a patient with said first portion covering the back of the patient's head and the upper portion of the back of the patient's neck and the second portion covering the top of the patient's head, the side edges of said first and second portions being secured to each other with said attachment elements.

5. A clean cap according to claim 4 including adhesive strips affixed to said first and second portions elliptical edges, the adhesive strips serving to adhere to the skin of the patient receiving the cap to retard blood passing underneath the cap.

6. A clean cap according to claim 4 including a third portion separate from said first and second portions, said third portion being defined by two opposed generally elliptical shaped edges and having attachment means affixed to the opposed intersections of said elliptical edges, the third portion being attachable to said first and second portions after they are formed on the head of a patient, the third portion fitting over the eyes and bridge of the nose of the patient.

* * * * *